United States Patent [19]

Brånemark et al.

[11] 4,330,891
[45] May 25, 1982

[54] ELEMENT FOR IMPLANTATION IN BODY TISSUE, PARTICULARLY BONE TISSUE

[76] Inventors: Per I. Brånemark, S-431 39, Mölndal; Bo Thuresson af Ekenstam, S-412 53, Göteborg, both of Sweden

[21] Appl. No.: 125,654

[22] Filed: Feb. 28, 1980

[30] Foreign Application Priority Data

Mar. 7, 1979 [SE] Sweden ................. 7902035

[51] Int. Cl.$^3$ .................... A61F 1/00; A61F 1/24
[52] U.S. Cl. ........................ 3/1; 3/1.9; 3/1.91; 128/92 C; 128/92 G
[58] Field of Search ............... 3/1.9–1.913, 3/1; 128/92 C, 92 CA, 92 G

[56] References Cited

U.S. PATENT DOCUMENTS

| 3,022,783 | 2/1962 | Tucker | 128/92 G |
| 3,605,123 | 9/1971 | Hahn | 3/1.9 |
| 3,767,437 | 10/1973 | Cruz, Jr. | 3/1.9 X |
| 3,919,723 | 11/1975 | Heimke et al. | 3/1.9 |
| 3,986,212 | 10/1976 | Sauer | 3/1.91 |
| 3,987,499 | 10/1976 | Scharbach et al. | 3/1.91 |
| 4,051,598 | 10/1977 | Sneer | 128/92 C X |
| 4,261,350 | 4/1981 | Branemark et al. | 128/92 CA X |

FOREIGN PATENT DOCUMENTS

| 2313678 | 10/1974 | Fed. Rep. of Germany | 3/1.9 |
| 2289160 | 5/1976 | France | 3/1.912 |
| 834256 | 5/1960 | United Kingdom | 128/92 G |

OTHER PUBLICATIONS

"Porous Metals as a Hard Tissue Substitute", by M. T. Karagianes, Biomat., Med. Dev., Art. Org., 1(1), pp. 171–181, 1973.

"Porous Metals as a Hard Tissue Substitute, Part II, Porous Metal Properties", by K. R. Wheeler et al., Biomat., Med. Dev., Art. Org., 1(2), pp. 337–348, 1973.

Primary Examiner—Ronald L. Frinks
Attorney, Agent, or Firm—Ostrolenk, Faber, Gerb & Soffen

[57] ABSTRACT

In an element for implantation in body tissue, particularly bone tissue, consisting of a biologically flawless material with a micro-pitted surface, the pores in the surface have a diameter many times smaller than has been previously known in order to permit the occurrence of such a tight and extensive boundary zone around the implanted element that this achieves reinforced and inextricable anchoring in the tissue. The pore diameter may be as little as about 10 nm and as large as a few multiples of the normal diameter of the cells in the tissue, preferably no larger than the cell diameter, i.e. about 1000 nm. Optimal results are obtained with pore diameters equal to or smaller than about 300 nm and a finely pored rutile layer has been found to give a particularly strong and durable joint with the growing tissue. Preferably at least one deposit of an agent facilitating and/or accelerating the growing-together process is arranged on or in the element. The element may be shaped with grooves, corrugations, channels etc. and be provided with an opening for tissue to grow through. The element is extremely suitable as anchoring device for a prosthesis or partial prosthesis and may be made integral therewith.

9 Claims, No Drawings

ELEMENT FOR IMPLANTATION IN BODY TISSUE, PARTICULARLY BONE TISSUE

The present invention relates to an element for implantation in body tissue, particularly bone tissue, in which the surface intended to face the body tissue is micro-pitted and the material of the element is selected to avoid the occurrence of unsuitable electrical potential differences and galvanic currents in the implantation region.

It is already known that with advances in surgical technique, and by suitable design of artificial implants, it is possible to achieve a more complete and permanent integration of an implant with the surrounding tissue.

It is of vital importance that improvements can be made to give a high frequency of successful operations with re-established biological function so that a second operation with the related traumatic consequences, both physiological and psychological, can can be avoided, thus also relieving unnecessary strain on the medical resources.

Swedish Patent application Ser. No. 77 10 777-9 emphasizes the importance of having the carrier elements or implants described therein so designed as to achieve rapid re-establishment of the blood circulation around and through the carrier means. This requires considerably increased supply of biological media with a reconstructive effect. This reduces the time for healing, due to increased cell formation and more rapid mineralization of in-growing tissue. A considerably improved clinical result and shortened hospitalization time are then achieved.

For this desired result, it is of vital importance that the prosthesis or connecting material is formed as an integratable part of the bio-physiological milieu and that this material is in a biologically, physically and biochemically optimal ratio to the bone tissue, which for the most part consists of $Ca^{2+}$, $PO_4^{3-}$ and $CO_3^{2-}$ ions with traces of other ionized substances occurring naturally in plasma or bone apatite.

Several research workers have stated that acceptable implantation has been obtained with a method as described for example by Wheeler et al in Biomet., Med. Dev. Art. Org., 1(2), 337–348 (1973) and by Karagianes in Biomet., Med. Dev. Art. Org., 1(1), 171–181 (1973). The experiments recorded include a couple of years experience with apes. However, the result of experiments on animals should be interpreted with the utmost caution since there are vast differences between the physical-biophysiological situation of homo and of other species, even within the primate group.

According to one interpretation of Wheeler et al and Karagianes, their good results are due to the use of titanium alloyed cylindrical fixtures produced in various ways with a pore size varying within the range of 275–650 μm. The theory of the method entails having the implanted cylinders larger in diameter than the cylindrical cavities drilled for them in the bone of laboratory animal jaw bones and inserting them by applying mechanical pressure.

However, the implantation of such carrier elements does not appear to give optimal and permanent ingrowth.

The object of the present invention is to effect a carrier element with improved properties as regards acceptance of the carrier element, primarily improved durability of the healthy ingrowth of the element due to its biological quality.

Accordingly, the present invention provides an element intended for implantation in body tissue, consisting of a biologically flawless material with a porous, i.e., micro-pitted surface intended to face the tissue in the implantation region of a patient, said material being selected to avoid the occurrence of unsuitable electrical potential differences and galvanic currents in the implantation region, wherein on or in the element is arranged at least one depot of at least one agent facilitating and/or accelerating the healing process of the body tissue on the element, wherein said agent contains enriched whole blood or plasma from the patient into whom the element is to be implanted by surgery.

An analysis of jaw implants in homo has unexpectedly shown that the operation results obtained are noticeably improved if the size of the micro-pitting approaches the order of magnitude of the cell diameter in the surrounding tissue or of a few multiples thereof. The normal cell size applicable is of the order of 1000 nm (where 1 nm = 10 Å). The bio-optimal result is achieved, however, if the pit diameter is selected within the range 10 to 300 nm, which is considerably smaller than the cell diameter. Material which can be used for prostheses and connecting devices should therefore have a micro-pitted surface. The surface between living, ingrowing cells and shoots to the cells in the mineralization process shall, together with channelized material and laminae with collagen fibrils, form such a tight and extensive boundary limit to the connecting devices that these achieve reinforced and inextricable anchoring in the living bone tissue. In this way, detachment of the implant from the boundary zone will be impossible. In experiments, it has been found that fracturing occurs away from established boundary zones.

The material for the connecting device should thus preferably have a surface structure in which the diameter of the pits should be 10 to 1000 nm, where the upper limit of 1000 nm corresponds to the cell diameter, or more preferably 10 to 300 nm where the upper limit of 300 nm corresponds to a transverse dimension of an offshoot from the tissue cell and of a fibril from bone tissue.

The mineralized constituents of the bone tissue are primarily hydroxy apatite having a composition $Ca_{10}(PO_4)_6(OH)_2$. This general formula for a minimum harmonic molecule unit corresponds to a unit length of about 5 to 20 nm. The mineralized parts of the bone tissue also include a certain amount of $Mg^{2+}$, $Na^+$ and $K^+$ as well as $CO_3^{2-}$, $Cl^-$, $F^-$ and citric acid. From the mineralogical point of view, this confirms good experience in operating in implants having a pit diameter of 10 to 300 nm.

The P atoms in $PO_4^{3-}$ are tetrahedrically interspersed and form a three dimensional, deformed network in which the $PO_4^{3-}$ ions are to a great extent connected by hydrogen bonds to the surrounding material of mineralized and living tissue consisting of proteins and other membrane substances such as carbohydrates, or fatty substances.

The upper limit (of the same order of magnitude as the cell diameter) and the lower, even more optimal, pit diameter limit correspond to the dimensions of the cell shoots and bone tissue fibrils with the mineral components as above.

The formation of new bone tissue takes place from the surface of the bone tissue through the living cell system with the intra-cellular matrix consisting of collagen fibres and inorganic components.

The inorganic components in the resulting bone constitute ⅔ of its weight. Of this, 85% comprises calcium phosphate and about 10% comprises calcium carbonate. The collagen fibres contribute greatly to the strength and elasticity of the bone tissue. All bone cells are of the same basic type, which undergo alterations at the same rate as the mineralization from osteoblasts via osteocytes to osteoclasts. Osteoclasts vary in appearance from cuboid to pyramid shapes oriented in continuous layers. The cytoplasma is characterized by the presence of ribonucleo protein which synthesizes protein components for the bone matrix. The osteoblasts contain the enzyme alkaline phosphotase which not only develops the matrix but is also responsible for the mineralization process. The osteoblasts are thereby transformed to osteocytes, fully developed bone cells, within the frame of the bone matrix. The cytoplasma of the osteoblasts contains fat, a certain amount of glycogen and fine granules. Direct contact between adjacent osteoblasts occurs during the bone building process. The process conserves a highly developed channel system for the exchange of metabolites between the bone cells and the vessel bed (the blood circulation).

The osteoclasts are a bone cell type, with wide variation in size, which can be found in the bone surface and consist of what are known as fused cells, giant cells having several cores. The surrounding bone tissue often appears to be partially demineralized and it is therefore assumed that this type of cell is a phase in the resorption of bone during the rebuilding phase.

In the bone matrix, the osteocollagen fibres are held together by a cement substance consisting substantially of mucopoly saccharides (chondroitin sulphate). The mineral substances of the bone are exclusively localized to the cement between the fibres and consist essentially of crystals of calcium phosphate of the hydroxy apatite type of crystal in the form of high density particles arranged perpendicularly to the osteocollagen fibres. The bone matrix is arranged in laminated form, the laminae having a thickness of 3 to 7 μm. The collagen fibres have transverse corrugation at a recurrent distance of 68 nm between the fibres. This confirms the correctness of the technical implementation of the material substitute to be selected as carrier element or replacement for traumatized tissue.

The mechanical or metallurgical production methods used should be such that both the number of micro-pits and the pit diameter in the material used gives it even greater total ingrowth surface between implant and newly formed tissue. It has also been found advantageous to provide the implant with large through openings for bone tissue to grow through.

Furthermore, the connecting devices shall be manufactured from biologically flawless material which cannot give rise to unsuitable differences in electrical potential or galvanic currents in the implant regions. Special materials such as titanium, titanium alloys, ceramic material or metal covered with ceramic material have been found to give acceptable biological integration.

Of the various materials which may be selected as starting material for optimally integratable connecting devices, titanium is, due to its proximity to Ca in the periodic table and its chemical inertness, supposed to be an extremely suitable basic material both as attachment device and prosthesis and also as replacement for soft tissue. Experiments have shown that no titanium has migrated into the surrounding tissue from unalloyed titanium implanted into various types of tissue by surgery.

The titanium material to be used for osteointegration should preferably be totally unalloyed, at least in the boundary zone between living tissue and implanted titanium.

The importance of the surface structure of the titanium material has been emphasized above, and in the case of titanium the surface structure is effected by scoring the surface with a cutting rate of less than 20 m/min under air or other oxygen gas cooling, such as $O_2$ or stabilized hydrogen superoxide. The cutting speed is kept low to give the process sufficient time to provide oxidization of the workpiece. The oxidization entails the formation of titanium oxides which, due to their mineralogical properties, promote the formation of a biologically appropriate surface structure of micropitted type (moon surface type).

Of course, the surface may be produced in some other manner, such as by sintering or metal vaporization in inert gas. However, the most economic method appears to be preparation with a cutting tool. The surface may also be ceramicized only with other biological, negatively charged ions such as phosphates (phosphatizing), phospates $+O_2$, and other combinations with small quantities of sulphate, fluoride, chloride and a certain basic carbonization.

When stored, titanium (and even low-alloyed titanium after machining) quickly acquires an oxidized surface equivalent to a crystallized surface of rutile $TiO_2$, whereupon the oxygen content of the titanium drops from the surface layer inwards until the oxygen content reaches a value of 0.

The deformed bone apatite tends to form strong bonds over its monocline and tetrahedrally (hexagonally) faceted structure with the finely pored rutile deposit of the titanium material, since the cubic molecule lattices of the rutile and the hexagonal molecule lattices of the bone apatite fit excellently together.

It is of the greatest importance that the healing process is given optimal opportunity with respect to (a) the substrate supplied, (b) enzyme activity and (c) mineralization.

This is achieved by providing the carrier element or connecting device, as well as the prosthesis material, with suitably located resorbable depots in ridges, punched recesses or applied surface layer. A combination of these alternatives may, of course, also be used. Between the fibres known as tropacollagen fibres, which can be seen as monomolecular conglomerate, there is a gap of 40 nm from the end of one fibre to the beginning of the next. The total collagen conglomerate consists of three collagen threads, each comprising a triple helix of osteotrope collagen fibres.

Dominant amino acids in the peptide chains of the collagen which are difficult to dissolve are glycine, about 30%, and proline. Such a peptide chain contains proline frequently peptidized with glycine. The proline is hydroxylated into a 4-stand by protocollagenhydroxylase. Vitamin C is required to accelerate the process. By means of a corresponding mechanism, some of the lower lysis content of the collagen is transformed to hydroxylysine. The hydroxy group of this amino acid is connected in a covalent bond with disaccharides consisting of galactose and glycose. The "fibre gap" described forms the centre for the mineralization of the bone tissue.

Experimental experience establishes the necessity of such a micro-pitted surface on the bone substitute material that in its network of pits, the pit diameter is so small that it can form three dimensional deposit points for (a) end terminal collagen fibre groups, (b) carbohydrate groups of the collagen and (c) collagen fibres with bone mineral while at the same time forming covalent bonds and inter-molecular binding forces in a network and space pattern which is as close as possible (5 to 500 nm). The prerequisites for a durable bond between living tissue and a substitute for living tissue are based on the relevant knowledge gathered about the collagen fibre system of the various types of tissue with interspersed minerals which have been specialized to the biological function of each tissue.

It is clear from the above which biological requirements must be met with respect to the aim of establishing a boundary zone, between living tissue and an implant, which is as firmly anchored as possible.

Over many years of experimental work, firm joints have been achieved with materials prepared in various manners, the surfaces of the connecting device being shaped with increased surface contact by means of corrugation and threading thereof.

By carefully screw-threading the fixture material, a healthy and strong bone surface is obtained with exact anatomical sealing congruence to the implant surface, thus giving a controlled compression of the bone tissue. Experience has shown that careful threading of drill-holes in the bone tissue and of the corresponding implant using cutting tools of titanium working at low speed gives the best seal and a greatly optimized and increased adhesion and healing surface between the implant and the living tissue prepared for operation, without producing any cuts in the tissue, for example due to metal particles which might be caused by other faster-working tools.

Swedish Pat. No. 77 10 777-9 describes an embodiment of the prosthesis and connecting devices permitting the application of depots either in or on them. Agents such as membrane effects, mineral substances, blood vessel dilator, coagulation-regulator, vitamins and growth-promoting hormones are incorporated in these depots. The agent may be applied to the material surfaces, or arranged in the form of suitably arranged depots consisting of fully resorbable material innocuous to the tissue. Another variant which has now been found by experiment to be able to improve the healing result is treating the material intended for operation by means of dipping, or some other form of surface contact, with whole blood or plasma possibly enriched before the operation with desired nutritional and therapeutic agents including desirable proenzymes, enzymes, hormones, specific substrates and vitamins.

The utilization of the principles described above for producing a carrier element according to the invention gives greatly improved results if the material having the required purity, shape, and surface structure (the latter determined in a scanning transmission electron microscope) is combined with depots of nutrients or is treated with enriched whole blood or plasma. It should be observed in this case that the patients' blood group and plasma quality have been adequately tested. Enriched blood or plasma from the patient himself is most advantageous to use.

The requirements specified, including the pit size, are applicable to all material selected for biological integration, for attachment devices for prostheses for use in the cranial bones, joints, soft tissue or soft tissue transition.

By implanting prosthetic appliances in the healing process to repair all types of tissue defects, regardless of whether these are the result of pathological processes or of traumatic influence, it is expected that all such healing processes will be strongly dependent upon biochemical reactions which guide the balancing of the control of the coagulation factors, the regrowth of the capillary bed, the addition of vital nourishing substances, and the provision of an adequate immunity. In the said Swedish patent application Ser. No. 7710777-9, the considerable importance of the prosthetic material has been stressed, and so have the healing properties of the living tissues. Thus, it has been strongly emphasised that the design and choice of all prosthetic material should be chosen carefully, with rigid requirements of the material which should constantly and functionally be accepted by the living tissue, whether soft or boney. Administration of growth-promoting substances may be general or local. In the case of local administration, four possible means of distribution are acceptable; these are:

1. Administration of growth-promoting substances orally by enrichment of the nutrition, both pre- and post-operatively.

2. In some cases, administration of growth-promoting substances by parenteral methods, both pre- and post-operatively.

3. The operative area can be treated locally by enrichment of the patient's own plasma or blood, or pre-analysed plasma may be considered adequate.

4. The prosthetic material may be treated before use with enriched plasma or whole blood. Irrespective of the nature of the prosthetic material, it should be given such a surface structure as to ensure an increased deposition of enriched plasma or whole blood.

The structure of the prosthetic material should enable such a quantitative deposition of biologically optimal growth factors, in order that these may be brought into the reconstructive area during the most intensive growth phase. Functional depots are formed in the prosthetic material in such a way that they may be used pre- or intra-operatively. The depots are manufactured of such materials which have been found to be immunologically acceptable and bio-degradable.

Thus either a biological material from treated patients, or certain selected plastics materials, may be used. Especially, bone, cartilage or collagen tissue from treated patients can be considered. The materials are preferably freeze-dried, whereafter enriched plasma or whole blood is added. Surplus material is removed and the above-mentioned depot can immediately be used, or may undergo a renewed freeze-drying procedure for later use. The depot areas in the prosthetic material are chosen in such a way that they are brought into intimate and adequate contact with tissues adjacent to the prosthesis.

Biologically important substances for general or local treatment or administration, include:

(a) amino acids, especially proline and glycine;

(b) blood factors balancing the coagulation ability;

(c) substances which positively affect the circulatory bed volume and oxygenation;

(d) vitamins, especially ascorbic acid and nicotinic acid compounds, whereby ascorbic acid is mandatory for a normal collagenisation;

(e) phosphate, primarily in the form of calcium phosphate with supplements by other materials such as sodium, potassium, magnesium, zinc, etc. (the phosphate ought to be completed by lesser amounts of chloride and fluoride ions);

(f) mesoinosite (an important substance which should be included);

(g) growth hormones are especially added to local depots or as finish on the prosthestic material, whereby fibrine is used as a covering layer;

(h) as protection against infection, broad-spectrum antibiotics are used and may be locally administered in the above described manner;

(i) enrichment by the depot principle, using leukocytes in excess and/or interferone.

The list of growth-biochemicals can naturally be added to, using the described method.

The above described technique can be further developed by compensating the need for substances promoting biological growth, using separate packages, or using pre-manufactured depots of different size, which may be stored before use in connection with reconstructive surgery. The packages containing sterile products should be hermetically sealed, to be opened just before the operation, or intraoperatively.

We claim:

1. An element intended for implantation in bone tissue consisting of a biologically flawless material selected to avoid the occurrence of unsuitable electrical potential differences and galvanic currents in the implantation region, said element having a, micro-pitted surface intended to face the tissue in the implantation region of a patient, said micro-pitted surface has pits with a diameter in the range of from about 10 nm up to about 1000 nm.

2. An element according to claim 1, wherein said element includes at least one depot of at least one agent beneficial to the healing process of the body tissue on the element, said agent containing at least one of whole blood and plasma of said patient into whom the element is to be implanted by surgery.

3. An element according to claim 1, wherein said material is titanium having a decreasing oxygen content from a titanium dioxide micro-pitted surface inwardly.

4. An element according to claim 2, wherein said at least one depot is within said element beneath the surface thereof.

5. An element according to claim 2, wherein said agent is selected from a group consisting of substances having membrane effects, mineral substances, blood vessel-dilating substances, coagulation-regulating substances, vitamins and growth-promoting hormones.

6. An element according to claim 1, 2 or 3, wherein the pit diameter is up to about 300 nm.

7. An element according to any one of claims 1 to 3, wherein the surface consists substantially of a fine-pitted rutile layer.

8. An element according to any one of claims 1 to 3, wherein the surface has at least one groove, corrugation, channel or recess roughening the surface.

9. An element according to any one of claims 1 to 3, wherein at least one through opening is provided for tissue to grow through, said opening arranged in the element and being many times greater than the pit diameter.

* * * * *